United States Patent [19]

Watmough

[11] Patent Number: 5,007,428

[45] Date of Patent: Apr. 16, 1991

[54] APPARATUS FOR EXAMINING A BODY OF LIVING TISSUES

[75] Inventor: David J. Watmough, Banchory, United Kingdom

[73] Assignee: The University Court of the University of Aberdeen, Aberdeen, United Kingdom

[21] Appl. No.: 424,252

[22] PCT Filed: Apr. 21, 1988

[86] PCT. No.: PCT/GB88/00302
§ 371 Date: Dec. 5, 1989
§ 102(e) Date: Dec. 5, 1989

[87] PCT Pub. No.: WO88/08272
PCT Pub. Date: Nov. 3, 1988

[30] Foreign Application Priority Data

Apr. 21, 1987 [GB] United Kingdom ............... 8709406

[51] Int. Cl.$^5$ .............................................. A61B 8/00
[52] U.S. Cl. ............................. 128/660.04; 128/664; 128/915
[58] Field of Search ............... 128/660.04, 664, 665, 128/915

[56] References Cited

U.S. PATENT DOCUMENTS

4,062,237 12/1977 Fox ................................. 73/861.25
4,398,540 8/1983 Takemura et al. ......... 128/661.04 X
4,545,387 10/1985 Bolique .......................... 128/664 X
4,651,744 3/1987 Bristow et al. ................ 128/660.01

Primary Examiner—Francis Jaworski
Attorney, Agent, or Firm—Rothwell, Figg, Ernst & Kurz

[57] ABSTRACT

An apparatus for the examination of living tissues, comprises an illuminator (228) for illuminating the tissue with infra-red-containing electromagnetic radiation, a television camera (202) for receiving the radiation which is transmitted through the tissue and image devices (216) for producing an image of the received radiation. In addition a probe (224) is provided for applying ultrasound to a region of the tissue and for receiving the reflected ultrasonic signals from the region. The signals obtained are representative of the velocity of blood flow in the region and a computer (216) is provided for generating from the signal an image which provides an indication of blood flow velocity in the region. The apparatus further comprises an arm rotatably mounted on a support about a pivot, the television camera (202) being mounted on the arm on one side of the pivot. A device for holding the tissue to be imaged by the television camera is mounted on the arm on the other side of the pivot.

6 Claims, 4 Drawing Sheets

APPARATUS FOR EXAMINING A BODY OF LIVING TISSUES

BACKGROUND OF THE INVENTION

The present invention relates to an apparatus for the examination of a body of living tissues. In particular, the present invention relates to an apparatus for telediaphanographic and ultrasonic investigation for use in the detection and diagnosis of cancer, and particularly breast cancer in women. The present invention further relates to an apparatus for imaging a body of living tissues.

It is now widely recognised that repeated use of X-ray mammography is valuable in the detection of breast cancer for women over 50 years but that in younger women aged less than 50 years where no benefits have been demonstrated the risk/benefit ratio is negative. In addition, in the young (<50 years) dense breast X-ray mammography misses a significant proportion of cancers and other tumours when used as a diagnostic technique. It is thus widely recognised that for screening and for diagnosis new, preferably more accurate and risk free techniques are desirable to detect breast cancer at an early stage before the disease is disseminated to other organs. The Forrest Report published in the United Kingdom in 1987 recommends screening at 3 yearly intervals by X-ray mammography of women over 50 years. The interval is chosen to minimise economic costs and to limit cumulative X-ray dose to breast tissues as it has been reported that X-rays can themselves cause cancer and that the breast is an especially sensitive organ.

GB-A-2092856, GB-A-2111794, U.S. Pat. No. 4,600,011 and EP-A-0108617 (each of which are in the name of the present applicant and the disclosures of which are incorporated herein by reference) relate to optical methods of detecting breast cancer (and other cancers) using optical (non-ionising) radiation but even these methods have only shown sensitivity of about 0.9 for palpable lesions. In other words about 10% of tumours are missed or wrongly interpreted.

It is also known to attempt to detect breast cancer by using Doppler ultrasound techniques. Two documents which disclose such techniques are "The Scattering of Ultrasound by Blood Flowing in Tumours" by P.N. Burns, PhD. Thesis, University of Bristol, 1985 and "Tumour Detection by Ultrasonic Blood Flow Signals" by P.N.T. Wells et al, (1977) Ultrasonics (15); p. 231-232. Such methods detect blood flow changes at the advancing front of breast carcinoma. The signals from the associated volume of neovascularization differ from those obtained when normal tissues are interrogated. The flow velocity and the quantity of blood flowing are generally higher near a malignant tumor. The ultrasound Doppler data is normally presented in an isometric display and comparison made of the signals close to and far away from the suspected tumour. When Doppler ultrasound is used by itself as a breast screening technique every cubic centimetre of tissue must be separately interrogated and analysed. With a single transducer (of area typically 1 cm$^2$) the method is very time consuming and required considerable computer memory, (typically more than provided by a microcomputer), to generate the isometric displays.

SUMMARY OF THE INVENTION

The present invention provides an apparatus for the examination of a body of living tissues, the apparatus comprising means for illuminating the body of living tissues with infra-red-containing electromagnetic radiation, means for receiving electromagnetic radiation which is transmitted through the body of living tissues, means for producing an image of the received radiation, means for applying ultrasound to a region of the body of living tissues, means for receiving reflected ultrasonic signals from the region, characterised by means for producing a signal which is representative of the velocity of blood flow in the region and means for generating from the signal a graphical representation which provides an indication of blood flow velocity in the region.

Preferably, the means for receiving electromagnetic radiation comprises a television camera and the apparatus further comprises a support, an arm rotatably mounted on the support about a pivot, the television camera being mounted on the arm on one side of the pivot, a holding device for holding the body of living tissues to be imaged by the television camera, the holding device being mounted on the arm on the other side of the pivot and a wavelength selector means for selecting the wavelength of infra-red radiation incident on the body of living tissues whereby the incident radiation is in a selected one of a series of pass-bands.

BRIEF DESCRIPTION OF THE DRAWINGS

An embodiment of the present invention will now be described by way of example only, with reference to the accompanying drawings, in which.

DETAILED DESCRIPTION OF THE PREFERRED EMBODIMENT

Figure 1:
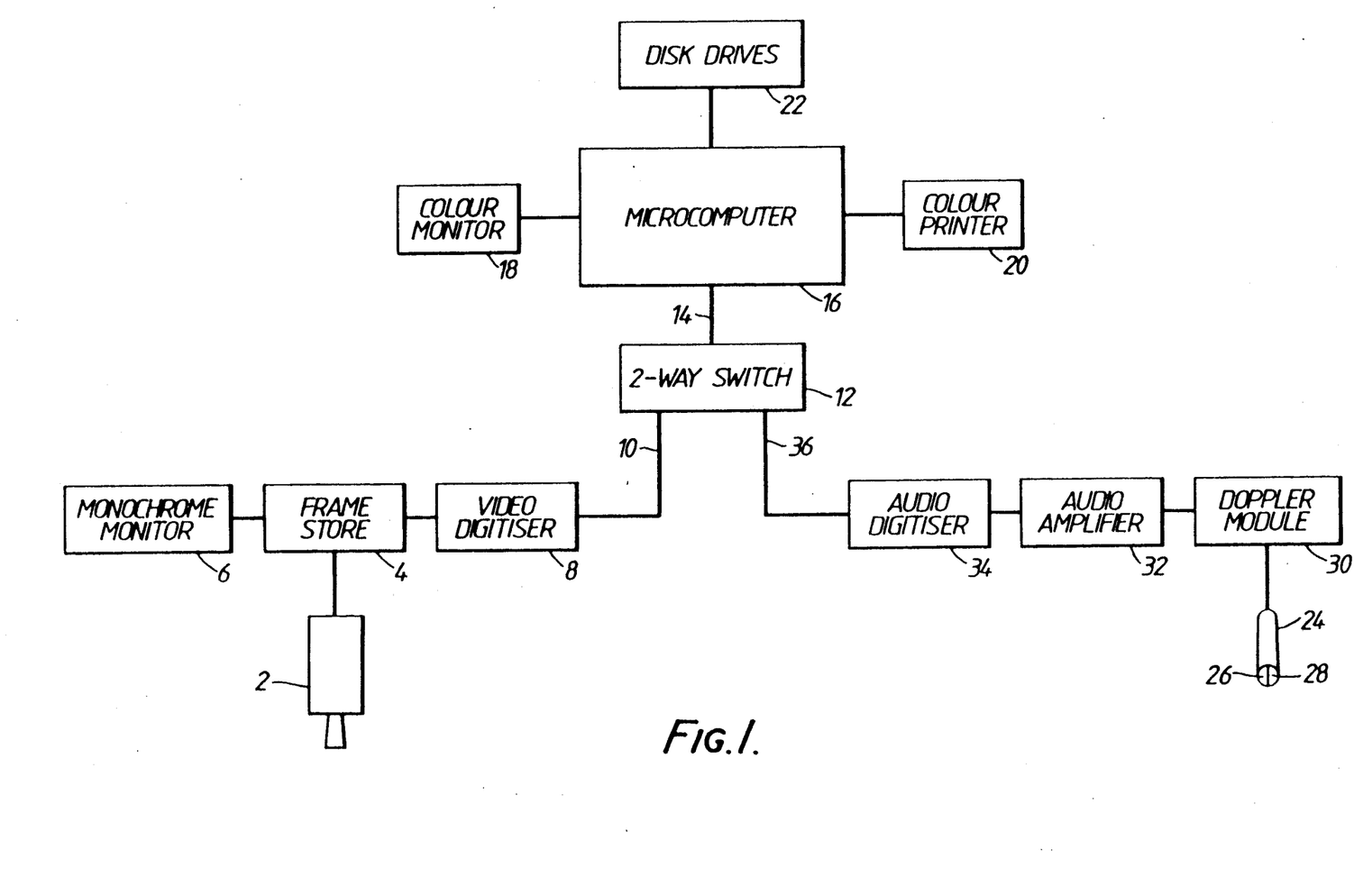
FIG. 1 is a diagrammatic illustration of part of an apparatus for examination of a body of living tissues in accordance with a first embodiment of the present invention.

Referring to FIG. 1, an apparatus for examination of a body of living tissues comprising a television camera 2 which is sensitive to wavelengths in the infra-red region of the electromagnetic spectrum, and in particular to the near infra-red. Typically, the camera 2 is sensitive to wavelengths ranging from 400 to 1200 nanometers. The camera 2 is connected to a frame store 4 which is adapted to store images which are received by the camera 2. A monochrome monitor 6 is connected to the frame store 4 and is adapted to display a monochrome image which is detected by the camera 2. A video digitiser 8 is also connected to the frame store 4. The video digitiser 8 is adapted to convert the analogue video signals which are stored in the frame store 4 into digital form for subsequent processing. The output of the video digitiser 8 passes to a first input 10 of a two way switch 12. The output 14 of the two way switch 12 is connected to a microcomputer 16 which is programmed to process the digital signals from the video digitiser 8, in a manner which is described in more detail below, and to produce colour-coded (pseudo-colour) images. Those images may be reproduced by a colour monitor 18 and/or a colour printer 20, both of which are connected to the microcomputer 16. One or more disk drives 22 are also connected to the microcomputer 16 for storage of image information.

The foregoing elements comprise a telediaphanographic system which can be used to image female breasts in the investigation of breast disease.

In accordance with the present invention, the telediaphanographic system is coupled with a Doppler ultrasound system for detecting malignant tumours in the female breast. The Doppler ultrasound system includes a Doppler ultrasonic transducer 24. The ultrasonic transducer 24 is cylindrical and is provided at one end thereof with a semi-circular ultrasonic transmitter 26 and a semi-circular ultrasonic receiver 28. The ultrasonic transmitter 26 is excited at its resonant frequency by an oscillator (not shown). The ultrasonic transducer 24 is connected to a Doppler module 30 which amplifies the received signal from the receiver 28 and produces a frequency difference signal (the Doppler signal) by mixing the received signal with the signal from the oscillator. The Doppler signal is outputted, in turn, to an audio amplifier 32 and an audio digitiser 34 which outputs a digital signal representing the Doppler shift and this digital signal is fed to a second input 36 of the two way switch 12. The two way switch 12 is adapted selectively to be switched between its two inputs 10, 36 depending on whether a telediaphanographic image or a Doppler image is to be displayed.

Figure 2:
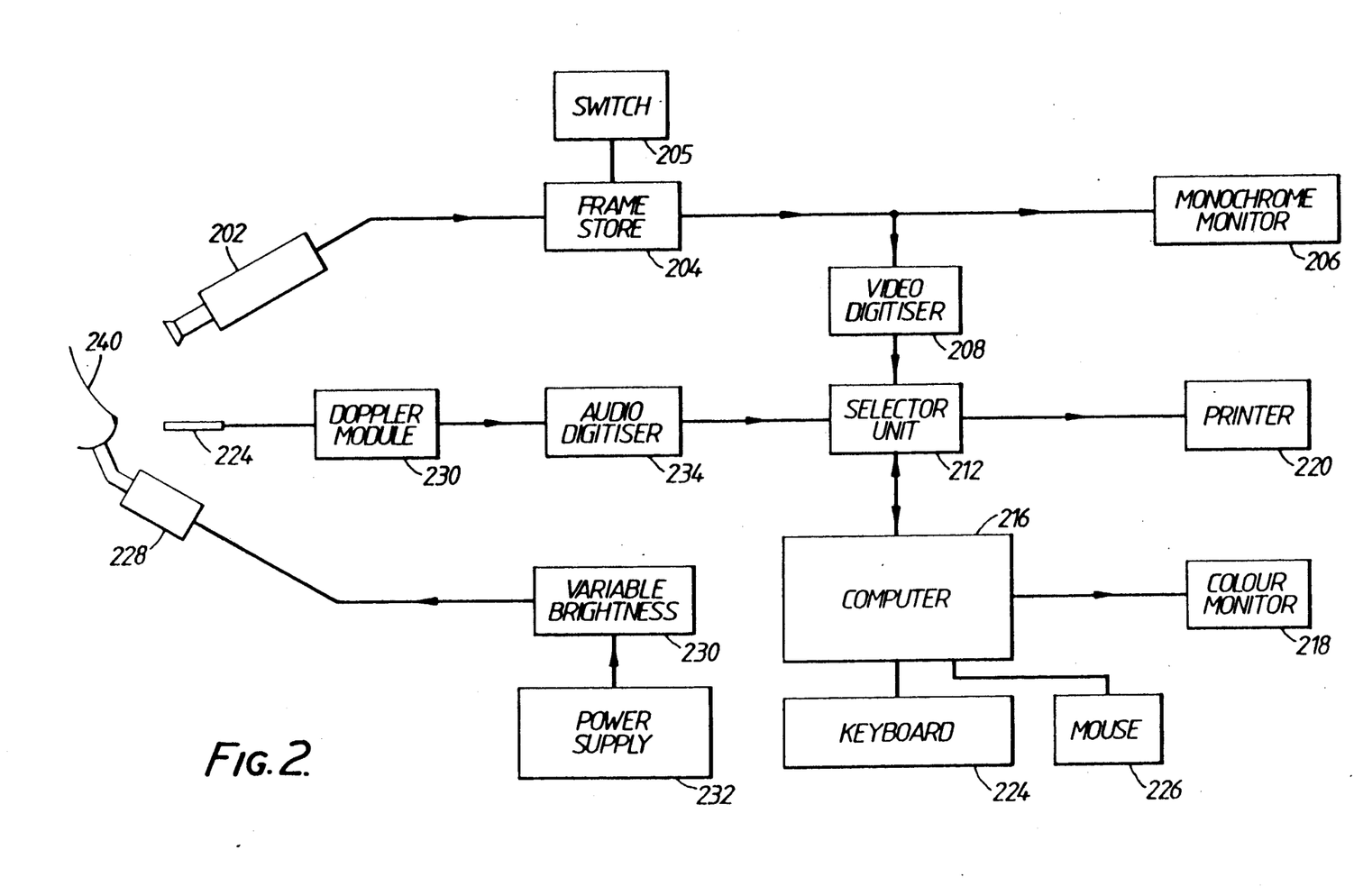
FIG. 2 is a diagrammatic illustration of an apparatus for examination of a body of living tissues in accordance with a second embodiment of the present invention.

FIG. 2 illustrates a second embodiment of an apparatus for examination of a body of living tissues. The apparatus comprises a video camera 202 which has a highly sensitive extended red (ER) Newvicon tube which permits imaging into the near infra-red region, up to 1000 nm, with good low light performance. The camera 202 may be provided with a zoom lens having a range from 17.5 mm to 105 mm. The camera 202 is connected to a frame store 204. The video signal from the camera 202 passes directly to the input of the frame store 204 and the signal is sampled in real time and held in a frame buffer of 512×512 pixels (8 bit/pixel). The frame buffer output is reconverted to an analog signal and is routed via a slow-scan converter to a monochrome monitor 206. An image in the frame store can be frozen by pressing a foot switch 205 which is a latching switch and must be pressed again to unfreeze the frozen image. A video digitiser 208 converts the analog output of the frame store 204 into a suitable digital form for input to the computer 216 via a selector unit 212. The video digitiser 208 employs a simple slow-scan system, together with proprietary software, and provides two conversion options (a) low resolution of 320×200 pixels, having a conversion time of 16 seconds, and (b) high resolution of 640×400 pixels having a conversion time of 45 seconds. A Doppler blood flow detector 224 together with its associated Doppler module 230 acts as a "stand alone" unit which is connected to an audio digitiser 234 which in turn is connected to the selector unit 212. The Doppler unit is powered from an internal rechargable battery. The Doppler module 230 includes a small loudspeaker (not shown) and in use the Doppler blood flow signals can be heard from the small loudspeaker. Amplification is provided by an AC coupled amplifier with variable feedback gain control. The low frequency cut-off is 300Hz and the gain range allows for an input signal from 400 mVpp to 6Vpp. The Doppler probe 224 operates at a nominal frequency of 8MHz and a power of less than 85 mW/cm$^2$. The maximum intensity in tissue is 64 mW/cm$^2$. The audio digitiser 234 acts to digitise the signal from the external Doppler blood flow detector. The maximum number of samples is limited to 80000. The sampling rate can be varied but the default value on start-up is 8000 samples per second, this giving an analysis range of from 0 to 4000 Hz which is adequate for most blood-flow velocities. A higher value may be chosen if frequency shifts greater than 4000 Hz are expected. The upper limit to sampling frequency is 20000, and the higher the sampling frequency the shorter the overall recording time. The audio digitizer 234 amplifies the signal and passes through a fourth order anti-alias filter (having a cut off at 8KHz) to an analog to digital converter. The resolution is 8-bit and the sampling frequency is selectable up to 20KHz. The selector unit 212 permits switching of a parallel port of the computer 216 between the video digitiser 208, the audio digitiser 234 and a printer 220 which is connected to the selector unit 212. In practice, the selector unit 212 incorporates the audio digitiser 234 with the audio input connector and an amplitude control. The computer 216 has a parallel port (not shown) which acts as an output port for the printer 220 and an input port for both the audio and video digitisers 234, 208. A colour monitor 218 is connected to the computer 216 and the computer 216 is also provided with a keyboard 224 and a mouse 226. The computer is provided with appropriate disc drives (not shown). The operation of the computer 216 is governed by software which controls all the functions of taking an image, storing it, and retrieving it for subsequent examination. The images taken are either video images or Doppler images. The software can either be adapted to give low resolution or high resolution images on the colour monitor 218 and on the printer 220. The software can also be adapted to given pseudo-colour images or greyscale images.

The apparatus also incorporate a torch 228 for transluminating the breast 240 of a patient. The torch 228 is connected to a variable brightness control 230 which in turn is connected to a suitable power supply 232. In practice, two torches are employed. One torch includes a heat absorbing filter and is intended for visual inspection of the tissues to be imaged by the camera. The heat absorbing filter permits the torch to be used for relatively long periods of time, i.e. up to about 5 minutes, while the operator examines the patient visually to determine whether or not there are any abnormalities in the breast. The second torch is not provided with a heat absorbing filter and is intended to be used for short periods of time only while the breast is being imaged by the camera 202. Each torch includes a quartz halogen lamp which emits high intensity radiation which includes infra-red radiation.

In use, the patient is seated and the camera 202 is arranged so that it is pointing at the breast 240 to be examined and is about 1.3 to 1.5 meters from the breast. The camera 202 is adjusted so that a good image of the breast appears on the monochrome monitor 206. A torch 228 which includes a heat absorbing filter is placed against the underside of the breast as shown in FIG. 2. The variable brightness control 230 is adjusted for maximum brightness and the breast is examined visually by the operator for any clear abnormality by moving the torch as required. If an abnormality is revealed, a second torch which does not include a heat absorbing filter is placed against the breast so as to illuminate the abnormality. The torch brightness control 230 and the lens aperture of the camera 202 are adjusted to obtain the best image on the monochrome monitor 206. The image in the frame store 204 is frozen by pressing the foot switch 205. The image on the monitor 206 may then be examined and this process may be repeated until an image suitable for recording is obtained. If desired, a photograph may be taken of the image on the monochrome monitor 206 by a camera (not shown). The stored image is then transferred to the computer by way of the video digitiser 208 and the selector unit 212, the latter being switched to an appropriate video position. The image is then stored on a floppy disc for the computer 216 and is shown on the colour monitor 218. The keyboard 224 may be employed to type in appropriate bibliographic information relating to the image. If a suspicious area of increased light absorption in the breast has been identified using the torches 228, the area can be further investigated using the Doppler probe 224. The selector unit 212 is switched to a Doppler position and the Doppler blood flow detector 224, 230 is switched on. Acoustic coupling jelly is applied to the end of the Doppler probe 224 and the tip is placed against the area of the breast to be investigated. The direction of the probe is adjusted until a distinctive, time varying sound is heard. If no such sound is heard then this suggests that there is no blood flowing in the region under investigation and that malignancy is unlikely. If a sound is obtained, the software of the computer is switched into Doppler mode and a Doppler spectrum can be displayed on the colour monitor 218 after appropriate analysis by the computer 216 of the digital signal from the audio digitiser 234. Initially, the Doppler signal is displayed on the colour monitor 218 in "oscilloscope" fashion. Then, the Doppler signal is analysed by the computer software using a Fast Fourier Transform Technique. The spectral analysis of the Doppler signal thereby produced is displayed on the monitor as a series of intensity against frequency graphs arranged in an isometric form to give a "3D" representation of the time course of the spectrum. Also displayed is a second representation of the Doppler signal wherein intensity is presented as a darkened area with frequency as the vertical axis and time as the horizontal axis. This is referred to as a "Velograph" display and is used to study the time-course of the maximum frequency. The Doppler data can be recorded on floppy disc for subsequent retrieval. In addition, the Doppler spectrum can also be printed by the printer 220.

Figure 3:
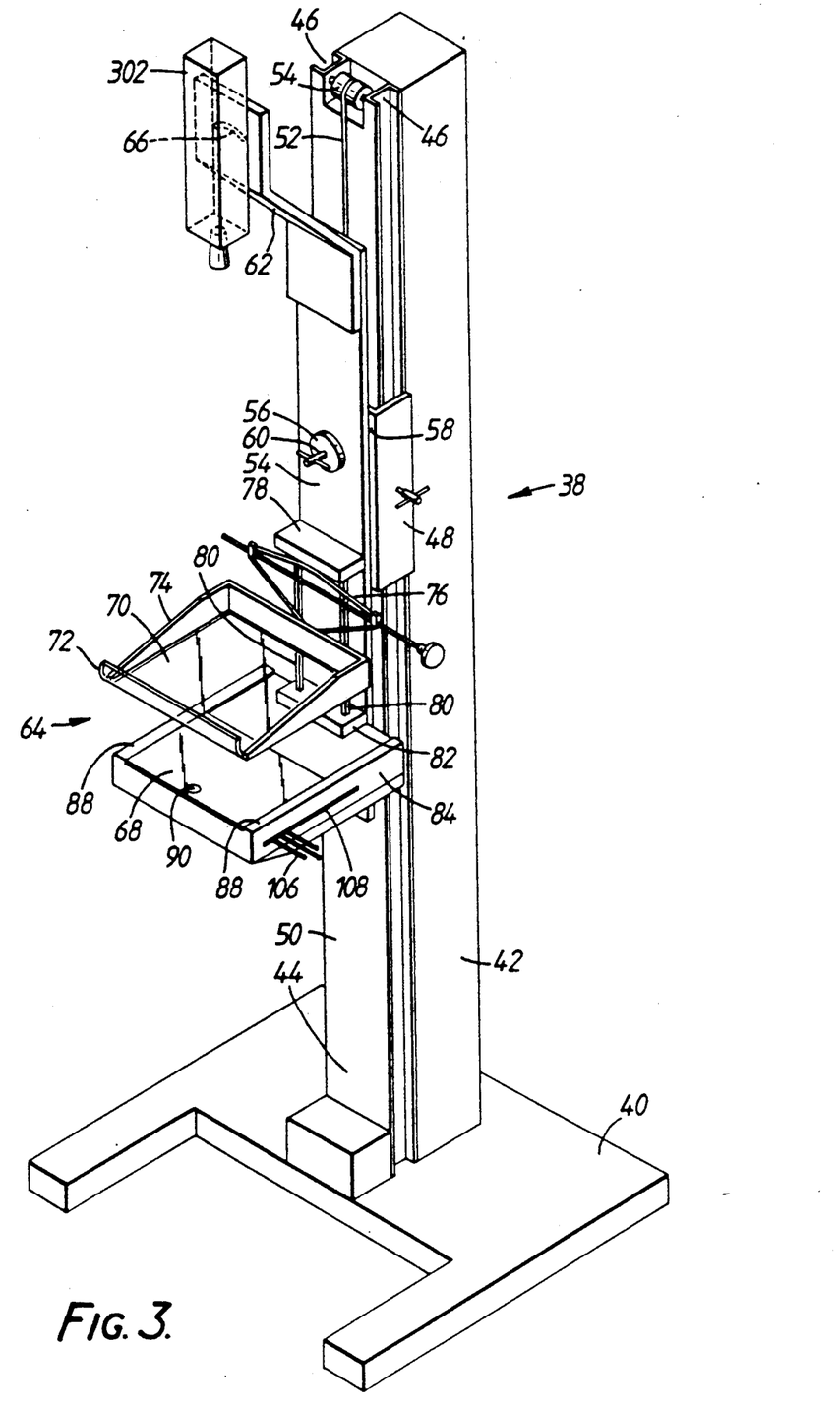
FIG. 3 is a perspective view of an imaging assembly of the apparatus for examination of a body of living tissues.

FIG. 3 shows an imaging assembly 38 which includes a television camera 302, which is sensitive to wavelengths in the near infra-red region of the electromagnetic spectrum and is the same as that illustrated in FIGS. 1 and 2, and an infra-red radiation source and also a device for holding the body of living tissues to be examined. The holding device is particularly adapted to hold a female breast for the purpose of breast scanning for detecting breast cancer.

The image assembly 38 includes a base 40, which permits the imaging assembly 38 to be free-standing, and an upright support 42 which is mounted on the base 40. One the front face of the support 42 is fixed a guide member 44 which has two opposed channels 46 therein which are provided on respective sides of the support 42. A sliding member 48, is slidably mounted on the front face 50 of the guide member 44 and extends into the opposed channels 46 so that the sliding member 48 is held captive on, but can freely slide up and down, the guide member 48. A wire 52 is fixed to the top of the sliding member 48, passes over a pulley 54 which is mounted at the top of the guide member 44 and extends downwardly into an elongate upright cavity between the guide member 44 and the support 42. A counterbalance weight (not shown) is attached to the free end of the wire 52. This counterbalance arrangement permits the sliding member 48 easily to be slid up and down the guide member 44. An arm 54 is mounted on a pivot 56 which is provided on the front face 58 of the sliding member 48. The pivot 56 is provided with a clamp 60 which permits the arm 54 to be clamped in any rotational position. The clamp 60 can be unclamped to permit the arm 54 to be freely rotated to any other desired rotational position. A camera mount 62 is provided at one end of the arm 54. The camera 302 is attached to the camera mount 62 and is directed towards a device 64 for holding the body of living tissues to be examined, the holding device being provided at the other end of the arm 54. The camera 302 can be moved over an arc 66 of about 5° so as to permit stereoscopic images to be obtained.

The device 64 for holding the body of living tissues to be examined is provided on the arm 54 on the other side of the pivot 56 and comprises a transparent bottom plate 68, which faces the camera 2 and whose distance from the camera 302 is fixed, and a transparent top plate 70 which is parallel to the bottom plate 68, is nearer to the camera 302 than the bottom plate 68, and can be moved towards or away from the bottom plate 68 thereby to vary the spacing between the two plates 68, 70. The top plate 70 is rectangular and includes an upwardly curved edge 72 which is remote from the support 42 and is adapted, in use, to bear against the chest of a female patient whose breasts are being examined. The top plate 70 is mounted in a 3-sided frame 74 which supports the other three sides of the top plate 70. The top plate 70 can be slid laterally out of the frame 74. The frame 74 is fixed to one end of a scissors jack 76, the other end of which is fixed to a mount 78 which is attached to the arm 54. A pair of parallel struts 80 extend between the mount 78 and a second mount 82 which is located adjacent the bottom plate 68. The frame 74 is slidably mounted on the struts 80. The top plate 70 can be moved towards and away from the bottom plate 68 by extending and compressing the scissors jack 76.

Figure 4:
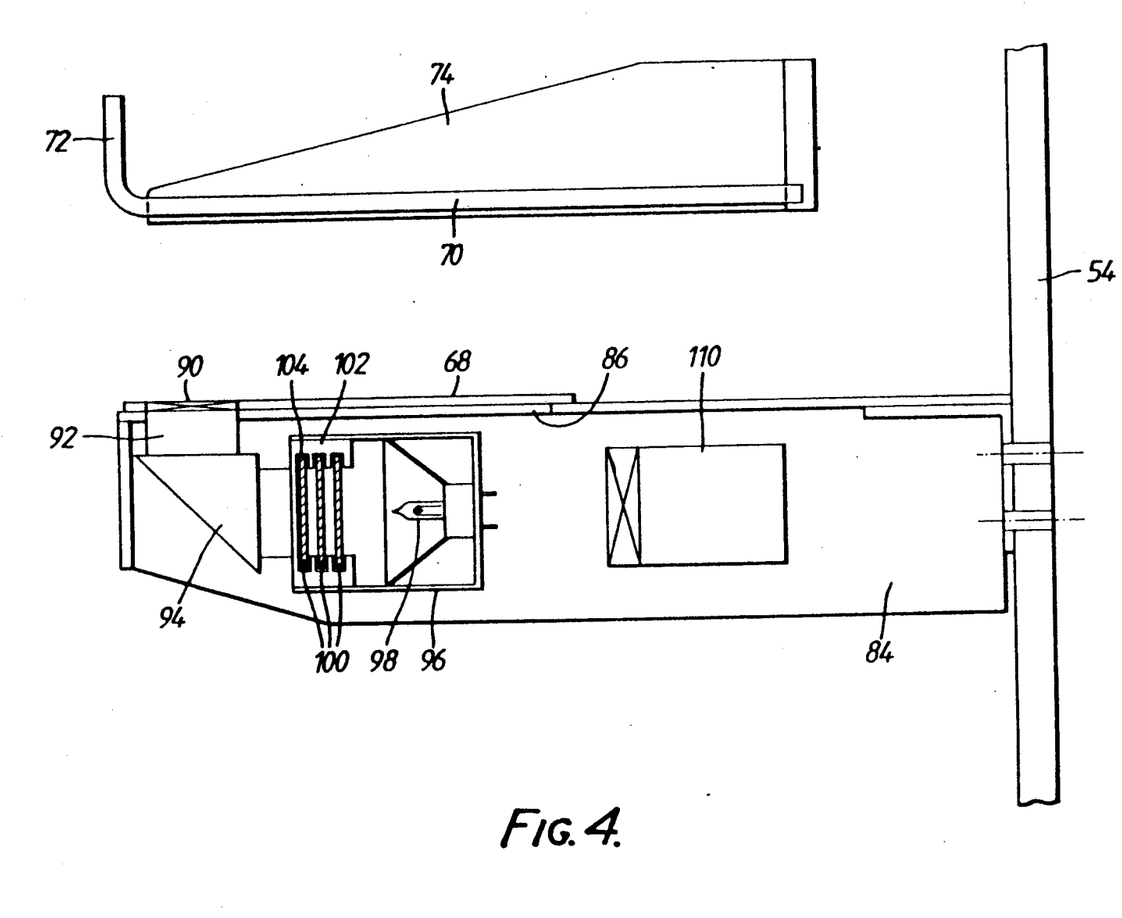
FIG. 4 is an enlarged cross-sectional view through an illumination system of the imaging assembly of FIG. 3.

The bottom plate is provided in the top of a housing 84 for an illumination system which is shown in greater detail in FIG. 3. The housing 84 is fixed to the arm 54 and includes an opening 86 in the upper surface thereof over which the bottom plate 68 is disposed. The bottom plate 68 is arranged to be slidable towards and away from the arm 54 by being held between two guide strips 88. A variable aperture 90 is provided in the bottom plate 68 and fixed to the bottom plate 68 beneath the variable aperture 90 is a light guide 92 which includes a prism, 94 preferably of perspex, which has a reflecting face at 45° to the bottom plate 68. At an input end of the light guide 92 is disposed a box 96 containing a source 98 of infra-red radiation and a series of filters 100. The source 98 of infra-red radiation may be a 12 volt light source or a laser having a wavelength range of 400 to 1200 nanometers, the laser optionally being tunable. The filters 100 are a series of spaced plates which are held by filter support 102. The filter support 102 has a plurality of pairs of opposed channels 104, each filter 100 being slidably mounted in a respective pair of channels 104. A respective handle 106 is attached to each filter 100 and the series of handles 106 extends out of the housing 84 through an elongate slot 108 which is parallel to the bottom plate 68. The handles 106 can selectively be slid in and out of the housing 84 thereby to position the respective filters 100 in front of or away from the source 98 of infra-red radiation. The handles 106 can also be slid along the slot 108 thereby to move the whole assembly of the bottom plate 68, the light guide 92, the box 96 containing the source 98 of infrared radiation and the filters 100 towards and away from the arm 54. A cooling fan 110 is also disposed in the housing 84 for removing warm air which has been heated by the source 98 of infra-red radiation.

It will be seen that by rotating the arm 54 the holding device 64 can be rotated to any desired position and this, coupled with the permitted movement of the illumination system towards and away from the patient by sliding of the handles 106 toward and away from the arm 54, permits the breast to be examined in any desired orientation. In addition, by varying the distance between the lower and upper plate 68, 70, a breast of any size can be firmly held between the plates 68, 70 for proper examination.

The operation of the apparatus of FIGS. 1, 3 and 4 will now be described, although it will be apparent that the following description also applies to the embodiment of FIG. 2. The patient stands in front of the imaging assembly 38 and a breast to be examined is placed between the two plates 68, 70 at the desired orientation and compressed therebetween by operating the scissors jack 76. The room is placed in darkness and then the source 98 of infra-red radiation is switched on. Filters 100 having passed bands around 100 nanometers wide are selectively placed in front of the source 98 of infra-red radiation so that the breast is illuminated with a succession of bands of infra-red radiation of increasing wavelength. This produces a succession of images, each of which is received by the camera 302 and recorded by the frame store 4. Each image is digitised by the video digitiser 8 and then the digitised signals are passed through the two-way switch 12 to the microcomputer 16 which processes the signals to produce a set of psuedo-colour images of the breast. These psuedo-colour images are combined to form a composite image which is displayed on the colour monitor 18, printed by the colour printer 20, and recorded on the disc drive 22.

The composite psuedo-colour image has dark areas which coincide with regions in the breast of increase infra-red absorption. Those regions may correspond to regions of carcinoma in the breast. However, dark areas may also indicate the position of a bruise or a blood filled cyst and this leads to ambiguities in the telediaphanographic results.

In order to resolve those ambiguities, and thereby accurately to diagnose the presence of cancerous regions, the top plate 70 is slid out of the frame 74 and the ultrasonic transducer 24 is placed on the breast. The ultrasonic transducer 24 can be accurately positioned over the suspected carcinoma by using the monochrome monitor 6 which shows an image of the dark region which is to be examined further and also an image of the ultrasonic transducer 24. When the ultrasonic transducer 24 is correctly positioned over the advancing front of the suspected tumour, the two-way switch 12 is switched over to input 36 and the microcomputer 16 is switched, if necessary, to a programme which processes digital signals from the audio digitiser 34.

The ultrasonic transducer 24 outputs a signal which is processed by the Doppler module 30, the audio amplifier 32 and the audio digitiser 34. The digital signal which is fed to the microcomputer 16 through the two-way switch 12 is representative of the frequency shift in the audio frequency range of the Doppler signal. The magnitude of the frequency shift is dependent upon the velocity of the red blood cells in the region which is being interrogated. In the vascular region around a tumour, the red blood cell velocity is relatively high and so there is a relatively large frequency shift. There is a distribution of velocities of the red blood cells and accordingly the digital signal which is fed to the microcomputer 16 is representative of data which has been sampled in a time domain. The microcomputer 16 analyses the data by Fourier transform analysis to produce an isometric display in which the Z axis represents the amplitude; the X axis represents the velocity of flow and the Y axis represents time. The isometric image is displayed on the colour monitor 18, printed out by the colour printer 20 as stored in the disk drives 22.

When an advancing front of a tumour is interrogated by the Doppler ultrasound apparatus, the amplitude and velocity demonstrate higher values in the isometric image than in normal tissues away from the tumour, this being due to higher red blood cell velocity in the vascular region of the advancing front of the tumour. The ultrasonic transducer 24 is then used to obtain an isometric image at a contra-lateral site on the patient, and by comparing the two isometric images obtained, one being at the periphery of the suspected lesion and the other being at the contra-lateral site, evidence may be obtained as to the nature of the lesion. The image at the contra-lateral site will show reduced amplitude and velocity if no tumour is present at the contra-lateral site.

The Doppler ultrasound system can detect regions of relatively high blood velocity, such as at the advancing front of tumours. However in bruises and blood filled cysts, such as those which may be present in female breasts and which are detected using telediaphanography, there is little or no blood flow and so these do not show up using Doppler ultrasound. Thus by combining telediaphonography and Doppler ultrasound interrogation procedures it is possible accurately to detect features such as tumours, cysts and bruises and to distinguish between malignant tumours and benign features such as bruises and cysts.

The ultrasonic detector 24 may be adapted to operate at varying ultrasonic frequencies, typically 4, 8 or 12 megahertz. Sensitivity of detection increases with increasing frequency but the penetration depth of the ultrasound into the body decreases with increasing frequency (i.e. the attenuation of ultrasound by the body is greater at higher frequencies). Accordingly, it is preferred to operate at 8 MHz in order to compromise between sensitivity and depth of penetration. However, for the examination of superficial lesions it may be preferable to use higher ultrasonic frequencies and conversely for deep lesions it may be preferable to use lower ultrasonic frequencies.

An advantage of the present invention is that it combines the two methods of telediaphanography and Doppler ultrasound to achieve a higher sensitivity and specificity for breast cancer than the known methods and also reduces the time taken for Doppler ultrasound investigation to typically less than one minute.

The optical, (telediaphanography) method is applied first to identify areas of increased light absorption which may be due to malignant disease or to, for example, bruising or a blood filled cyst. These latter conditions may lead the clinician wrongly to conclude that a bruise indicates a malignant change within the tissues.

If there is not a malignant change within the tissues interrogation with Doppler Ultrasound of the same region of tissues, thus identified, does not produce an abnormal isometric display and thus a bruise or other non-malignant condition is correctly indicated. Without the use of an optical telediaphanograpic method (prior to ultrasonic Doppler interrogation) the entire breast volume would have to be sampled with the Doppler probe and any bruise, being a region where there is no moving blood, would fail to be defined.

The preferred embodiment of the present invention also provides a compressor system which can compress the breast tissues at any angle and which utilises light in pass-bands typically 100 mm wide between 300 and 1200 nm. The breast tissues are held stationary while a series of optical filters are interposed in the optical beam. A television camera, sensitive particularly in the near infra-red part of the electromagnetic spectrum, rapidly detects a series of images which are digitised and displayed superimposed on a television monitor in different colours. Different pathologies are represented in the images by colour/shade variations. The advantages of the arrangement are that small lesions are better resolved during compression and that the period of image digitisation may be several seconds. This process obviates the need for (costly) very rapid image capture. The optical filters may be engaged under software control from the same microcomputer which displays images and analyses ultrasound data. When an image of a lesion is thus identified a Doppler transducer, typically operating at 8MHz, is placed on the skin overlying the advancing front of the tumour and audio signals generated by the blood flow recorded. These are digitised and used to generate isometric displays of blood flow velocity as a function of time and amplitude of flow. By this combined method lesions are located and information about associated blood flow changes obtained all in the space of a few minutes. By way of comparison a Doppler study with a single small transducer would take much longer to produce definitive results and in any event would miss lesions where no abnormal flow occurred (e.g. bruising or a cyst).

The combined approach disclosed herein which employs a telediaphanographic interrogation coupled with a Doppler ultrasound interrogation is quicker and more comprehensive then either method alone and can provide required screening and diagnostic procedures particularly in the case of the young dense breast.

The present invention can provide a light-guided Doppler system which can achieve early detection and improved diagnosis of diseases (primarily) of the female breast.

It employs a novel combination of two previously distinct techniques in the one instrument which can substantially contribute to the accuracy of diagnosis without the intrinsic hazards associated with X-Ray Mammography.

The system of the present invention can be employed as a complementary technique to X-Ray Mammography rather that a direct substitute. However following more extensive clinical trials it may prove to be superior in a number of pathologies and for certain subject groups.

As a result of the inventor's investigation, it is believed there are a number of areas where the present invention may be more acceptable than X-Ray Mammography.

(1) Radiologically dense breasts
(2) Young subjects
(3) Breasts with scar tissue
(4) Silicone augmented breasts
(5) Repeated follow-up subsequent to treatment
(6) Discharge from the nipple
(7) Subjects who refuse X-Ray
(8) Where the outcome of X-Ray is ambiguous
(9) Pregnant subjects
(10) Discrimination between benign and malignant tumours, cysts, bruises and haematoma.

Although primarily intended as an instrument for the detection and diagnosis of breast disease, the technique may also be applicable to other anatomical areas which are translucent in the visible and near infra-red spectrum.

It is also possible with the apparatus of the present invention to interface an electronic stethoscope with the 2-way switch or selector unit. The electronic stethoscope could be either additionally connected to the 2-way switch or selector unit or substituted for the Doppler unit after the Doppler signals have been recorded. In use, if audible Doppler signals are obtained from an interrogated region of the breast, the electronic stethoscope could subsequently be used to detect characteristic sounds of malignant tumours in that same region.

I claim:

1. An apparatus for the examination of a body of living tissues, the apparatus comprising means for illuminating the body of living tissues with infra-red containing electromagnetic radiation, means for receiving electromagnetic radiation which is transmitted through the body of living tissues, means for producing an image of the received radiation, means for applying ultrasound to a region of the body of living tissues, means for receiving reflected ultrasonic signals from the region, characterised by means for producing a signal which is representative of the velocity of blood flow in the region and means for generating from the signal a graphical representation which provides an indication of blood flow velocity in the region.

2. An apparatus according to claim 1 wherein the means for applying ultrasound and the means for receiving reflected ultrasonic signals comprises an ultrasonic Doppler bloodflow detector.

3. An apparatus according to claim 1 or claim 2 further comprising a switching device to which the said means for receiving electromagnetic radiation and the said means for receiving reflected ultrasonic signals are connected, and a computer which is connected to the switching device, the switching device being selectively switchable between the said two receiving means thereby to select which of the said two receiving means is connected to the computer.

4. An apparatus according to claim 3 wherein the computer is adapted to process digital signals from the switching device and wherein the means for producing an image and the means for generating a graphical representation comprise a common video monitor which receives processed signals from the computer.

5. An apparatus according to claim 3 wherein the means for receiving electromagnetic radiation comprises a television camera which is sensitive to infra-red radiation and wherein the television camera is connected to the switching device by a frame store and a video digitiser.

6. An apparatus for the examination of a body of living tissues according to claim 1 wherein the means for receiving electromagnetic radiation comprises a television camera, and wherein the apparatus further comprises a support, an arm rotatably mounted on the support about a pivot, the television camera being mounted on the arm on one side of the pivot, a holding device for holding the body of living tissues to be imaged by the television camera, the holding device being mounted on the arm on the other side of the pivot and a wavelength selector means for selecting the wavelength of infra-red radiation incident on the body of living tissues whereby the incident radiation is in a selected one of a series of pass-bands.

* * * * *